United States Patent
Barbuzzi et al.

(10) Patent No.: US 6,696,050 B2
(45) Date of Patent: *Feb. 24, 2004

(54) HAIR TREATMENT COMPOSITIONS

(75) Inventors: Elena Maria Gabriella Barbuzzi, Merseyside (GB); Wolfgang Robert Bergmann, Chicago, IL (US); Cheryl Anne Taylor, Merseyside (GB); Stephen Lee Wire, Merseyside (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/135,972

(22) Filed: Apr. 30, 2002

(65) Prior Publication Data

US 2003/0012757 A1 Jan. 16, 2003

(30) Foreign Application Priority Data

Apr. 30, 2001 (EP) .............................. 01303915

(51) Int. Cl.$^7$ ............................... A61K 7/075
(52) U.S. Cl. ............. 424/70.11; 424/70.1; 424/70.19; 424/70.21
(58) Field of Search ............. 424/70.1, 70.11, 424/70.19, 70.21, 70.27

(56) References Cited

U.S. PATENT DOCUMENTS 4,801,445 A   1/1989  Fukui et al.
6,083,491 A * 7/2000  Mellul et al. ............... 424/63

FOREIGN PATENT DOCUMENTS

| EP | 0224378 A2 | 6/1987 |
| EP | 0478326 A1 | 4/1992 |
| JP | 10/114622 | 5/1998 |
| WO | 01/30310 | 5/2001 |

OTHER PUBLICATIONS

Harry's Cosmeticology by Ralph Harry, pp431–432 and 506–508(1982).*
International Search Report Application No. PCT/EP 02/04515 mailed Sep. 23, 2002.
Chemical Abstracts, vol. 129, No. 1, (7/98) to Matsumoto et al. "cosmetic Stock Compositions for Hair Preparation and Skin Makeup" –XP 002185547 & JP 10 114622 A assigned to Toshiba Silicone Co.

* cited by examiner

Primary Examiner—Jyothsna Venkat
(74) Attorney, Agent, or Firm—Milton L. Honig

(57) ABSTRACT

This invention relates to an aqueous hair treatment comprising coated particles comprising a solid core having a D3, 2 average particle size in the range from 10 to 700 nm, and a coating polymer covalently bonded to the solid core. Use of the coated particles in a hair treatment composition to impart body to the hair is also described.

13 Claims, No Drawings

HAIR TREATMENT COMPOSITIONS

FIELD OF THE INVENTION

This invention relates to rinse-off hair treatment compositions and to their use in the treatment of hair.

BACKGROUND AND PRIOR ART

Shampoo compositions are generally formulated with highly effective cleansing surfactants, typically anionic surfactants, and do not in themselves provide much conditioning or styling benefit to the hair. In fact, basic shampoo formulations which have not been supplemented with be specific conditioning or styling agents have a tendency to leave the hair in a cosmetically-unsatisfactory condition with regards to manageability and stylability. The hair tends to have a harsh, dull and dry feel, often referred to as "creak", is often difficult to comb, in either the wet or the dry state, typically has poor brushing properties, and tends to have poor set-retaining abilities.

This has resulted in the use of products containing specific conditioning and/or styling agents. Such agents are generally applied separately after shampooing and rinsing the hair, for example, in the form of conditioner formulations or styling mousses etc. Alternatively, conditioning and/or styling agents have been incorporated into the shampoo formulations. Although the latter approach provides the advantage of removing the need for a separate conditioner or styling treatment, the conditioning and/or styling agents are not always compatible with the shampoo ingredients, especially the anionic surfactant. This can result in the cleansing action and/or cosmetic benefit being compromised.

One of the most common methods for imparting styling benefits to the hair has been the use of hair fixative agents, such as high molecular weight polymers. The problem with using such agents is that they have a tendency to negatively impact on conditioning attributes such as wet and dry stage clean feel and smoothness. In fact, they can result in a sticky feel to the hair.

Conventional styling polymers are typically water soluble. This means that when incorporated into a shampoo or conditioner which is rinsed off the hair, there is a tendency for the styling polymer to be washed away to a greater or lesser degree with the shampoo/conditioner. Hence, most styling products are leave-in products which are applied to the hair as lost-shampoo/conditioner treatments.

The problem being addressed by the present invention is the provision of rinse-off hair treatment compositions which impart styling benefits, and in particular body benefits on the hair, but which do not compromise the cleansing action of the shampoo and which do not negatively impact on the conditioning attributes of the hair. The body benefits or attributes the present invent on is looking particularly to provide are root lift, increased hair volume, bounce, control (i.e. ease of styling) and manageability, i.e. maintenance of style without undue stiffness and negative sensory feel. Such body attributes are particularly attractive to people with fine or long, weighty hair.

One way in which this problem has been addressed in the past has been to include conditioning agents, for example silicones and cationic surfactants, in the compositions, to counter the negative effects of the styling agents. Although such conditioning agents do provide substantial improvements in for example the wet and dry combing properties of the hair and in the smoothness of the hair, they tend to have a negative effect on many of the attributes associated with hair body.

An alternative approach has been the use different forms of styling agents such as small particulate materials. Such an approach is described, for example, in our unpublished PCT international Patent Application No. PCT/GB00/04020. This document describes the use of small hard particles, and in particular colloidal silica, in hair treatment compositions to impart body and volume to the hair. Although providing significant styling benefits, the use of these materials can still lead to small levels of sensory negatives, such as for example a dry feel to the hair.

JP 10144622 (Toshiba Silicone) discloses cosmetic compositions containing from 0.5 to 50 wt % of particles consisting of colloidal silica cores surrounded by silicone shells which may be used on the skin or hair. Hairdressing lotions, hair creams and cleansing compositions such as a shampoo, rinse and conditioner are disclosed as suitable cosmetic compositions in which the particles can by utilised. In the treatment of hair, they are described as providing a flexible and smooth feeling and as having good set-retaining ability. There is no teaching that the particles provide significant body benefits, such as volume, root lift and bounce, to the hair.

We have now found that the inclusion of a certain level of small solid particles covalently grafted with a polymer which comprises other structural units which are not silicone-based in conventional hair treatment formulations provides substantial styling benefits, in particular with regards to imparting body attributes to the hair. Furthermore, the conditioning attributes of the hair are not adversely affected by the use of hair compositions containing these particles and there is no necessity to incorporate additional conditioning agents or specialised surfactant systems. The compositions of the present invention are also stable.

The incorporation of the small particles covalently grafted with polymer into the hair treatment compositions of this invention leads to substantive improvements in the body of the waster and optionally conditioned hair, especially if a subsequently styling regime is follower. The compositions impart body attributes, such as are root lift, volume, bounce and manageability, in the absence (or substantial absence), of a styling polymer, which leads to compositions which have a styling benefit, but nevertheless do not suffer from the sensory negatives (e.g. stickiness and/or dry feel) which are associated with prior styling compositions which are based on, for example, a styling polymer.

DEFINITION OF THE INVENTION

Accordingly, this invention provides an aqueous hair treatment composition comprising coated particles comprising (a) a solid core having a D3, 2 average particle size in the range from 10 to 700 nm, and (b) a coating polymer covalently bonded to the solid core.

Additionally, this invention provides for the use of coated particles as defined above in a hair treatment composition to impart body.

DETAILED DESCRIPTION AND PREFERRED EMBODIMENTS

Definitions

Unless specified otherwise, all wt % values quoted hereinafter are percentages by weight based on total weight of the hair treatment composition.

As used hereinafter, the term "coated particle" refers to a particle comprising a solid core having a D3, 2 average particle size in the range 10 to 700 nm which is coated, via covalent grafting, with a coating polymer, the polymer forming a coating or shell around the solid core.

As used hereinafter, the term "solid core" or "solid core particle" refers to the solid core of the coated particle.

As used hereinafter, the term "coating polymer" or "polymer coating" refers to the polymer covalently grafted to the solid core of the coated particle which polymer comprises one or more polymerised monomeric or oligomeric structural units in which at least one of the monomeric or oligomeric units is not a silicone unit, i.e. a silicone, siloxane or silane unit.

As used hereinafter, the term "water-insoluble", means that the material is soluble in distilled water at a concentration of less than 0.01 g/l, preferably less than 0.001 g/l at 20° C.

As used hereinafter, the term "aggregates" refers to secondary particles which are a collection of primary particles which have been fused to form face to face sintered structures which cannot be dissociated, and as such are relatively hard.

$D_{3,2}$ average droplet or particle sizes as referred to herein may be measured by means of a laser light scattering technique, using a 2600D Particle Sizer from Malvern Instruments.

COATED PARTICLES

The coated particles are present in the conditioner composition in an amount of from 0.01 to 10, preferably from 0.01 to 5, more preferably from 0.05 to 3, yet more preferably from 0.05 to 2.5, and most preferably from 0.1 to 1 wt %. In particular, it has been found that levels of coated particles of 0.5 wt % or less work particularly well in the compositions of the present invention.

The coated particles comprise solid cores having D3, 2 average particle sizes in the range from 10 to 700 nm, the solid cores being coated with a coating polymer which is covalently bonded to the solid core.

Preferably the D3, 2 average particle size of the coated particles is in the range from 20 to 1000, more preferably from 20 to 800, yet preferably from 50 to 500 and most preferably from 50 to 250 nm.

Sufficient coating polymer is grafted so as to form a effective shell around the solid core. Suitably, the weight ratio of the solid core to the coating polymer is in the range from 20:1 to 1:10, preferably from 20:1 to 2:3, more preferably from 20:1 to 1:1, more preferably from 10:1 to 1:1, yet more preferably from 5:1 to 1:1, and most preferably from 5:1 to 2:1. A particularly preferred ratio is about 4:1.

Although coated particles that are sparingly soluble may be employed in hair treatment compositions of the invention, it is highly preferred that the coated particles be water-insoluble.

SOLID CORE

The solid core particles have a D3, 2 average particle size in the range from 10 to 700, preferably from 10 to 500, more preferably from 20 to 300, yet more preferably from 20 to 200, and most preferably from 30 to 150 nm, for example about from 50 to 100 nm.

It is preferred that the solid core particles be colloidal in an aqueous dispersion.

The solid core can be a primary particle or an aggregate, so long as its satisfies the size requirement specified above. Preferably, it is a primary particle.

Suitably, the solid core particles are relatively hard and typically have a Youngs Modulus of more than 0.01, preferably more than 0.1, more preferably more than 1.0, yet more preferably more than 4 GPa, and yet more preferably more than 10 GPa.

The solid core material can be organic or inorganic in nature. Furthermore, the solid core may be composed entirely of one material or may consist of a composite of materials.

Suitable organic solid particles can be made by a variety of methods including:

(i) via the synthesis of (co)polymers as described in, for example, Breiner et al. (1998) *Macromolecules*, Vol. 31, 135; and (ii) via the synthesis of cross-linked polymer structures as described in, for example:
Ishizu & Fukutomi (1988) *J. Polym. Sci., Part C: Polym. Lett.*, Vol. 26, 281;
Saito et al. (1990) *Polymer*, Vol. 31, 679;
Thurmond et al. (1997) *J. Am. Chem. Soc.*, Vol. 119, 6656; and
Stewart & Liu (2000) *Angew. Chem. Int. Ed.*, Vol. 39, 340).

Suitable inorganic solid particles can be prepared by techniques such as:

(i) precipitation, as described in, for example, Matjievic (1993) *Chem. Mater.*, Vol. 5, 412;

(ii) dispersion, as described in, for example, Stober et al. (1968) *J. Colloid Interface Sci.*, Vol. 26, 62; and Philipse & Vrij (1989) *J. Colloid Interface Sci.*, Vol. 129, 121);

(iii) microemulsion processes, as described in, for example, Baumann et al. (1997) *Adv. Mater.*, Vol. 9, 995; and (iv) sol-gel processes, as described in, for example:
Forster & Antonietti (1998) *Adv. Mater.*, Vol. 10, 195;
Kramer et al. (1998) *Langmuir*, Vol. 14, 2027;
Hedrick et al. (1998) *Adv. Mater.*, Vol. 10, 1049;
Zhao et al. (1998) D. *Science*, Vol. 279, 548; and
Ulrich et al. (1999) *Adv. Mater.*, Vol. 11, 141.

Examples of suitable solid core materials for use as the solid cores include polymers, which are preferably cross-linked, (e.g. polystyrene, silicone elastomer powders, PTFE, rubber), silicas, alumina, alumin silicate, clays and colloidal metals (e.g. titanium dioxide, zinc oxide).

One preferred class of material is PTFE. PTFE solid core particles may be composed entirely of PTFE polymer or may consist of a composite of PTFE polymer and one or more further polymers such as polyethylene. Suitable PTFE particles are further described in our unpublished copending United Kingdom Patent Application Nos. GB 0012064.2 and GB 0012061.8.

Another preferred class of materials are silicas, such as silica gels, hydrated silicas and precipitated silicas (e.g. Cab-O-Sil and Aerosil).

A particularly preferred class of solid core materials are the colloidal silicas. Suitable examples include Ludox MS-40, Ludox SM, Ludox CL and Ludox AM.

Suitably, the solid core amounts to from 95 to 5 wt % preferably from 95 to 40, more preferably from 90 to 50, and most preferably from 90 to 60 wt %, for example about 80 wt %, of the total weight of the coated particles.

Solid cores that are either water-insoluble or only sparingly soluble in water may be employed in the preparation of coated particles. Preferably, the solid core is water-insoluble.

COATING POLYMER

The coating polymer is a polymer which is covalently bonded to the solid core.

Suitably, the coating polymer amounts to from 5 to 95, preferably from 10 to 60, more preferably from 10 to 50, and most preferably from 10 to 40 wt %, for example about 20 wt %, of the total weight of the coated particles.

Suitably, the molecular weight of the coating polymer is no greater than 500,000, preferably no greater than 250,000, more preferably no greater than 200,000, yet more preferably no greater than 150,000 and yet more preferably no greater than 100,000 Daltons. The molecular weight may be lower than 50,000 or even lower than 25,000 Daltons.

Suitably, the molecular weight is at least 500, preferably at least 1,000, more preferably at least 2,000 and yet more preferably at least 5,000 Daltons.

The coating polymer is tethered to the surface of the solid core particle by one or more covalent bonds, although other secondary means of attachment such as hydrogen bonding and absorption may also be present. The coating polymer may be bonded via its terminal end(s) and/or via side-chains in the polymer chain. Preferably at least 70 wt %, more preferably at least 80 wt % and yet more preferably at least 90 wt % of the coating polymer present in coating on the solid core is covalently bonded to the solid core surface.

More than one coating polymer may be used to coat the solid core. The coating polymer cannot consist entirely of silicone structural units. It must comprise at least one monomeric or oligomeric unit which is not a silicone unit. Thus the polymer can be a block copolymer made up, for example of siloxane and styrene units.

In a preferred embodiment, the coating polymer is substantially free of silicone. By substantially free is meant that silicone units (i.e. blocks) account for less than 10, preferably less that 5 wt % of the overall weight of the coating polymer.

Suitable coating polymers may be cationic, anionic, amphoteric or nonionic in nature.

Examples of suitable anionic polymers include copolymers of vinyl acetate and crotonic acid, terpolymers of vinyl acetate, crotonic acid and a vinyl ester of an alpha-branched saturated aliphatic monocarboxylic acid such as vinyl neodecanoate, copolymers of methyl vinyl ether and maleic anhydride (molar ratio about 1:1) wherein such copolymers are 50% esterified with a saturated alcohol containing from 1 to 4 carbon atoms such as ethanol or butanol, acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and biphenyl acrylate); glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide); and other compatible unsaturated monomers.

Examples of suitable amphoteric polymers are polymers which contain cationic groups derived from monomers such as t-butyl aminoethyl methacrylate as well as carboxyl groups derived from monomers such as acrylic acid or methacrylic acia.

Examples of suitable nonionic polymers are homopolymers of N-vinylpyrrolidone and copolymers of N-vinylpyrrolidone with compatible nonionic monomers such as vinyl acetate. Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PBP K-90 and homopolymers of N-vinylpyrrolidone having an average molecular weight of about 1,000,000 sold under the name of PVP K-120. Other suitable examples of nonionic polymers are homopolymers and copolymers of styrene.

Examples of suitable cationic polymers are copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

PREPARATION OF COATED PARTICLES

The coated particles are preferably prepared as an aqueous pre-emulsion, which can then be mixed with other ingredients to form the hair treatment composition.

Different methods of preparation may be used depending of the size of coated particles required. Suitably, the coated particles can be prepared as follow:

(i) "Large" Coated Particles

Larger coated particles, for example having a D3, 2 average particle size of at least 100 nm and which employ solid core particles having D3, 2 average particle size of at least 50 nm, can be prepared in an aqueous polymerisation system in which the solid core particles are mixed with water, an emulsifying surfactant, polymeric units and a suitable polymerisation catalyst. The resulting aqueous emulsion of coated particles can be directly incorporated into a hair treatment composition.

(ii) "Small" Coated Particles

Smaller coated particles, for example having a D3, 2 average particle size of less than 100 nm and which employ solid core particles having D3, 2 average particle size of less than 50 nm, tend to have to be prepared by an alternative organic polymerisation system in which the solid core particles are mixed with polymeric units in an organic solvent, free of any surfactant. The resulting coated particles are typically precipitated out of the organic solvent, washed and redispersed in water as an aqueous emulsion with a suitable emulsifying surfactant.

Polymeric Units

The coating polymer is suitably prepared by polymerisation of the component monomers or oligomers described above.

Where the polymer contains silicone units, the solid core particles are preferably mixed with organosiloxane units having 2–10 silicon atoms and containing no hydroxyl groups and being of unit formula (II):

$$R^1{}_n SiO_{(4-n)/2} \qquad (I)$$

in which $R^1$ is a hydrogen atom or a substituted or unsubstituted hydrocarbon group.

A cross-linking agent such as a silane compound having a functional group may be added to the organosiloxane component for the polymer coat so as to improve the strength of the polymer shell.

Examples of suitable organosiloxane component units which can form part of the coating polymer are as follows:

(i) Cyclic compounds such as hexamethyl cyclotrisiloxane, octamethyl cyclotetrasiloxane, decamethyl cyclopentasiloxane, 1,3,5,7-tetramethyl-1,3,5, 7-tetraphenyl cyclotetrasiloxane, 1,3,5,7-tetrabenzyltetramethyl cyclotetrasiloxane and 1,3,5,7-tris(3,3,3-trifluoropropyl)trimethylsiloxane;

(ii) Cyclic organosiloxanes containing an organic functional group such as trimethyl triphenyl cyclotrisiloxane, tris(3,3,3-aminopropyl) tetramethyl cyclotetrasiloxane, 1,3,5,7-tetra[N-(2-aminoethyl)-3-aminopropyl] tetramethyl cyclotetrasiloxane, 1,3,5,7,-tetra(3-mercaptopropyl) tetramethyl cyclotetrasiloxane and 1,3,5,7,-tetra(3glycidoxypropyl) tetramethyl cyclotetrasiloxane.

iii) Cyclic and linear organosiloxanes having an ethylenically unsaturated group such as 1,3,5,7-tetra(3-methacryloxypropyl) tetramethyl cyclotetrasiloxane, 1,3,5,7-tetra(3-acryloxypropyl) tetramethyl cyclotetrasiloxane, 1,3,5,7-tetra(3-carboxypropyl) tetramethyl cyclotetrasiloxane, 1,3,5,7-tetra (vinyloxypropyl) tetramethyl cyclotetrasiloxane, 1,3,5, 7,-tetra(vinyloxyethoxypropyl) tetramethyl tetracyclosiloxane, 1,3,5,7-tetra(p-vinylphenyl) tetramethyl cyclotetrasiloxane, 1,3,5,7,-tetra[1-(m-vinylphenyl)methyl] tetramethyl cyclotetrasiloxane, 1,3,5,7,-tetra[2(p-vinylphenyl)ethyl]tetramethyl cyclotetrasiloxane, 1,3,5,7-tetra[3-(p-vinylphenoxy) propyl] tetramethyl cyclotetrasiloxane, 1,3,5,7,-tetra[3-(p-vinylbenzoyloxy)propyl tetramethyl tetracyclosilaoxane, 1,3,5,7,-tetrea[3-(p-isopropenylbenzoylamino)propyl] tetramethyl tetracyclosiloxane, 1,3,5,7,-tetra(N-methacryloyl-N-methyl-3-aminopropyl) tetramethyl cyclotetrasiloxane, 1,3,5,7,-tetra(N-acryloyl-N-methyl-3-aminopropyl) tetramethyl cyclotetrasiloane, 1,3,5,7,-tetra[N,N-bis (methacryloyl)-3-aminopropyl] tetramethyl cyclotetrasiloxane, 1,3,5,7-tetra[N,N-bis(acryloyl)-3-aminopropyl] tetramethyl cyclotetrasiloxane, 1,3,5,7-tetravinyl tetramethyl cyclotetrasiloxane, octavinyl cyclotetrasiloxane, 1,3,5-trivinyl trimethyl cyclotrisiloxane, 1,3,5,7-tetraallyl tetramethyl cyclotetrasiloxane, 1,3,5,7-tetra(5-hexenyl) tetrametnyl cyclotetrasiloxane, 1,3,5,7-tetra(7-oxenyl) tetramethyl cyclotetrasiloxane and 1-(p-vinylphenyl)-1,1-diphenyl-3-diethoxy disiloxane.

Examples of suitable silane compounds which may be added to the organosiloxane component for the polymer coating so as to improve the strength of the polymer shell are as follows:

(i) Silane compounds having an organic functional group such as 3-aminopropylmethyl dimethoxysilane, 3-aminopropyltrimethoxysilane, N-(2-aminoethyl)-3-aminopropyl trimethoxysilane,N-triethylenediaminepropylmethyl dimethoxysilane, 3-glycidoxypropylmethyl dimethoxysilane, 3,4-epoxycyclohexylethyl trimethoxysilane, 3-mercaptopropyl trimethoxysilane, trifluoropropyl trimethoxysilane and 3-carboxypropylmethyl dimethoxysilane.

(ii) Silane compounds having an ethylenic unsaturated group such as 3-acryloxypropyl triethoxysilane, 3-methacryloxypropyl trimethoxysilane, (vinyloxypropyl)methyl dimethoxysilane, (vinyloxyethoxypropyl)methyl dimethoxysilane, p-vinylphenylmethyl dimethoxysilane, 1-(m-vinylphenyl)methyldimethyl isopropoxysilane, 2-(p-vinylphenyl)ethyldimethoxysilane, 3-(p-vinylphenoxy) propylmethyl dimethoxysilane, 1-(p-vinylphenyl) ethylmethyl methoxysilane, 1-(o-vinylphenyl)-1,1,2-trimethyldimethoxydisilane, m-vinylphenyl[(3-triethoxysilyl)propl] diphenylsilane, [3-(p-isopropenylbenzoylamino)propyl] diphenyldipropoxysilane, N-methacryloyyl-N-methyl-3-aminopropylmethyl dimethoxysilane, N-acryloyl-N-methyl-3-aminopropylmethyl dimethoxysilane, N,N-bis (methacryloyl-3-aminopropyl methoxysilane, N,N-bis (acryloyl)-3-aminopropylmethyl dimethoxysilane, N-methacryloyl-N-methyl-3-aminopropylphenyl diethoxysilane, 1-methacryloylpropyl01,1,3-trimethyl-3,3-dimethoxydisiloxane, vinylmethyl dimethoxysilane, vinylethyl diisoproposysilane, allylmethyl dimethoxysilane, 5-hexenylmethyl diethoxysilane and 3-octenylethyl diethoxysilane.

Any of the organosiloxanes or silanes can be used either singly or as a mixture of two or more organosiloxanes and/or silanes.

Besides the above-mentioned silicones, linear or branched organosiloxane oligomers may also be used as an organosiloxane containing an organic functional group or an ethylenic unsaturated group. In the case of such organosiloxane oligomers, although there is no particular limitation for the terminal group of the molecular chain terminal is sequestered by an organic group other than a hydroxyl group such as an alkoxy group, trimethylsilyl group, dimethylvinylsilyl group, methylphenylvinylsilyl group, methyldiphenylsilyl group and 3,3,3-trifluoropropyldimethylsilyl group.

In forming the coating polymer, any of the polymeric units may be used either singly or as a mixture of two or more units, with the proviso that silicone units cannot be used exclusively.

Emulsifying Surfactant

Any surfactant materials either alone or in admixture may be used as emulsifiers in the preparation of the pre-emulsions of coated particles. Suitable emulsifiers include anionic, cationic and nonionic emulsifiers.

Examples of anionic emulsifiers are alkylarylsulphonates, e.g., sodium dodecylbenzene sulphonate, alkyl sulphates e.g., sodium, lauryl sulphate, alkyl ether sulphates, e.g., sodium lauryl ether sulphate nEO, where n is from 1 to 20 alkylphenol ether sulphates, e.g., octylphenol ether sulphate nEO where n is from 1 to 20, and sulphosuccinates, e.g., sodium dioctylsulphosuccinate.

Suitable cationic surfactants are well-known to the person skilled in the art. Preferably, the cationic surfactant contains a quaternary ammonium group. Suitable examples of such cationic surfactants are described hereinbelow in relation to conditioning surfactants present in conditioner compositions. Particularly preferred as cationic emulsifying surfactants are C6–20, preferably C8–18, monoalkyl and dialkyl quaternary ammonium compounds.

Examples of nonionic emulsifiers are alkylphenol ethoxylates, e.g., nonylphenol ethoxylate nEO, where n is from 1 to 50, alcohol ethoxylates, e.g., lauryl alcohol nEC, where n is from 1 to 50, ester ethoxylates, e.g., polyoxyethylene monostearate where the number of oxyethylene units is from 1 to 30.

Preferably, at least one anionic surfactant or cationic surfactant is present as an emulsifying surfactant.

(i) Aqueous Polymerisation System

In this process, the solid core particles are mixed with water, an emulsifying surfactant, a polymeric unit and a suitable polymerisation catalyst. Preferred methods for preparing coated particles according to this system are described in JP 10114622.

Any catalyst may be used so long as it is capable of polymerising a low-molecular polymeric unit in the presence of water. Suitable catalysts include those commonly used for polymerisation of low-molecular organosiloxanes such as a mixture of hydroxylated aliphatic sulphonic acid with an unsaturated aliphatic sulphonic acid, an aliphatic hydrogen sulphate, an aliphatic substituted benzenesulfonic acid, hydrochloric acid, sulphuric acid, phosphoric acid.

Certain anionic surfactant emulsifiers have a weak catalytic action such can be used in conjunction with a polymerisation catalyst. Such anionic surfactants include sodium dodecylbenzenesulphonate, sodium octylbenzenesulphonate, ammonium dodecylbenzenesulphonate, sodium lauryl sulphate, ammonium lauryl sulphate, triethanolamine lauryl sulphate, sodium tetradecenesulphonate and sodium hydroxytetradecenesulphonate.

Cationic surfactant emulsifiers can also have a weak catalytic action and, therefore, it is preferred to use them together with a polymerization catalyst such as an alkaline metal hydroxide (e.g., lithium hydroxide, sodium hydroxide, potassium hydroxide, potassium hydroxide, rubidium hydroxide and caesium hydroxide).

The amount of water used in the emulsification is typically from 50 to 500, preferably from 100 to 300 parts by weight to 100 parts by weight of the total amount of the coated particles component in the emulsion. The solid concentration in the emulsion is typically from 20 to 70, preferably from 30 to 60 wt % of the total weight of the emulsion. The temperature of preparation of the emulsion (i.e. for the condensation reaction) is typically in the range from 5 to 100° C.

The amount of emulsifying surfactant in the emulsification is typically from 0.5 to 50, preferably from 0.5 to 20 parts by weight of the total amount of the coated particles component in the emulsion.

The amount of polymerization catalyst in the emulsification is typically from 0.05 to 10 parts by weight of the total amount of the coated particles component in the emulsion.

As already mentioned, a preferred solid core material of the present invention is colloidal silica. In the emusification step, this is present as an aqueous dispersion with $SiO_2$ as the basic unit of the solid core particles. Ordinarily, colloidal silica is classified into acidic and alkaline subclasses based upon its characteristics and any of them may be appropriately selected and used depending upon the condition for the emulsification polymerisation. When using acidic silica, the emulsifying surfactant should be an anionic surfactant, and conversely, when using an alkaline silica, the emulsifying surfactant should be a cationic surfactant, in order to keep the silica in a stable state.

(ii) Organic Polymerisation System

In this process, the solid core particles are mixed with a polymeric unit in an organic solvent, free of any surfactant. The resulting coated particles are typically precipitated out of the organic solvent, washed and redispersed in water with a suitable emulsifying surfactant to form an aqueous emulsion. Preferred methods for preparing coated particles according to this system are described in Pyun et al. (2001) *Polym. Prepr. (Am. Chem. Soc., Div. Polym. Chem.)*, Vol. 42(1), 223.

A suitable method for preparing "smaller" coated particles, for example in which the solid core particles have a D3, 2 average particle size of 10 to 20 nm. is a microemulsion process. An example of a suitable microemulsion process for the preparation of silica solid cores coated with silicone polymer is as follows. Silica colloid is prepared in an aqueous medium (e.g. 6 mM NaOH) by the reaction of methlytrimethoxysilane within micelles in the presence of an emulsifying surfactant (e.g. a quaternary ammonium cationic surfactant). The presence of the surfactant around the particles prevents large-scale flocculation. In order to prevent the colloid particles aggregating via residual surface silanol groups, the surface silanol groups of the silica colloid are silylised. Firstly, whilst still in the aqueous medium, surface silanol groups are reacted with methoxytrimethylsilane to generate trimethylsilyl groups. The particles are then precipitated into an appropriate organic solvent (e.g. methanol) to remove the surfactant, and subsequently redispersed in an appropriate organic solvent (e.g. tetrahydofurnan). The transfer from aqueous to organic solvent is necessary to achieve complete silylisation of the surface silanol groups and thus obtain stable colloids. Any residual silanol groups are deactivated and 2-bromoisobutyrate groups incorporated onto the surface of the particles by reacting the colloid particles in an appropriate organic solvent with 3-(2-bromoisobutyryloxy)-propylchlorodimethylsilane and 1,1,1,3,3,-hexamethyldisilazane. The functionalised silica colloids can then be purified by precipitation, e.g. in methanol, and dialysis in acetone. The functionalised silica colloids are then coated by reaction with polymeric units in an atom transfer radical polymerisation (ATRP) to form coated particles.

The coated particles are finally precipitated out of the organic solvent, for example, into methanol, washed (e.g. with acetone) and redispersed in water with a suitable emulsifying surfactant to form an aqueous pre-emulsion of coated particles.

If the final hair treatment product in which the coated particles are to be incorporated contains as its primary surfactant a cationic surfactant, it is preferred that the emulsifying surfactant is a cationic surfactant. Thus when using silica as the solid core, preferably alkaline silica is used. The coated particle emulsion prepared using cationic surfactant as the emulsifying agent has been found to produce conditioner formulations which are particularly stable.

Alternatively, if the final hair treatment product in which the coated particles are to be incorporated contains as its primary surfactant a anionic surfactant, it is preferred that the emulsifying surfactant is an anionic surfactant. Thus when using silica as the solid core, preferably acidic silica is used. The coated particle emulsion prepared using anionic surfactant as the emulsifying agent has been found to produce shampoo formulations which are particularly stable.

The pre-emulsions of the coated particles have a tendency to be either acidic or alkaline in nature. In order to keep them stable over a long period, they are neutralised by adding alkali or acid. Examples of suitable alkali neutralising agents are sodium hydroxide, thorium carbonate, thorium bicarbonate and triethanolamine. Examples of suitable acidic neutralising agents are hydrochloric acid, sulphuric acid, nitric acid, acetic acid and oxalic acid.

HAIR TREATMENT COMPOSITIONS

Compositions in accordance with the invention are formulated as compositions for the treatment of hair and subsequent rinsing.

SHAMPOO COMPOSITIONS

A particularly preferred hair treatment composition in accordance with the invention is a shampoo composition.

Such a shampoo composition will comprise one or more cleansing surfactants which are cosmetically acceptable and suitable for topical application to the hair. Further surfactants may be present as an additional ingredient if sufficient for cleansing purposes is not provided as emulsifier for the silicone component. It is preferred that shampoo compositions of the invention comprise at least one further surfactant (in addition to that used as emulsifying agent for the silicone component) to provide a cleansing benefit.

Suitable cleansing surfactants, which may be used singularly or in combination, are selected from anionic, amphoteric and zwitterionic surfactants, and mixtures thereof. The cleansing surfactant may be the same surfactant as the emulsifier, or may be different.

Anionic Cleansing Surfactant

Shampoo compositions according to the invention will typically comprise one or more anionic cleansing surfactants which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in shampoo compositions of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, sodium. lauryl ether sulphate(n)EO, (where n ranges from 1 to 3), ammonium lauryl sulphate and ammonium lauryl ether sulphate(n)EO, (where n ranges from 1 to 3).

Mixtures of any of the foregoing anionic cleansing surfactants may also be suitable.

The total amount of anionic cleansing surfactant in shampoo compositions of the invention is generally from 5 to 30, preferably from 6 to 20, more preferably from 8 to 16 wt %.

Co-surfactant

The shampoo composition can optionally include co-surfactants, to help impart aesthetic, physical or cleansing properties to the composition.

A preferred example is an amphoteric or zwitterionic surfactant, which can be included in an amount ranging from 0 to about 8, preferably from 1 to 4 wt %.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cccamidopropyl betaine and sodium cocamphopropionate.

Another preferred example is a nonionic surfactant, which can be included in an amount ranging from 0 to 8, preferably from 2 to 5 wt %.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in shampoo compositions of the invention include the $C_{10}$–$C_{18}$ N-alkyl ($C_1$–$C_6$) polyhydroxy fatty acid amides, such as the $C_{12}$–$C_{18}$ N-methyl glucamides, as described for example in WO 92 06154 and U.S. Pat. No. 5,194,639, and the N-alkoxy polyhydroxy fatty acid amides, such as $C_{10}$–$C_{18}$ N-(3-methoxypropyl) glucamide.

The shampoo composition can also optionally include one or more cationic co-surfactants included in an amount ranging from 0.01 to 10, more preferably from 0.05 to 5, most preferably from 0.05 to 2 wt %. Useful cationic surfactants are described hereinbelow in relation to conditioner compositions.

The total amount of surfactant (including any co-surfactant, and/or any emulsifier) in shampoo compositions of the invention is generally from 5 to 50, preferably from 5 to 30, more preferably from 10 to 25 wt %.

Cationic Polymer

A cationic polymer is a preferred ingredient in shampoo compositions of the invention, for enhancing conditioning performance of the shampoo.

The cationic polymer may be a homopolymer or be formed from two or more types of monomers. The molecular weight of the polymer will generally be between 5000 and 10000000, typically at least 10000 and preferably in the range 100000 to about 2000000. The polymers will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd editon. The ratio of the cationic to non-cationic monomer units is selected to give a polymer having a cationic charge density in the required range.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic conditioning polymers can comprise mixtures of monomer units derived from amine- and/or quaternary ammonium-substituted monomer and/or compatible spacer monomers.

Suitable cationic conditioning polymers include, for example:

- copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);
- copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);
- cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;
- mineral acid salts of amino-alkyl esters of homo-and co-polymers of unsaturated carboxylic acids having from 3 to 5 carbon atoms, (as described in U.S. Pat. No. 4,009,256);
- cationic polyacrylamides (as described in WO95/22311).

Other cationic conditioning polymers that can be used include cationic polysaccharide polymers, such as cationic cellulose derivatives, cationic starch derivatives, and cationic guar gum derivatives. Suitably, such cationic polysaccharide polymers have a charge density in the range from 0.1 to 4 meq/g.

Cationic polysaccharide polymers suitable for use in compositions of the invention include those of the formula:

A—O—[R—N$^+$(R$^1$)(R$^2$)(R$^3$)X$^-$], wherein: A is an anhydroglucose residual group, such as a starch or cellulose anhydroglucose residual. R is an alkylene, oxyalkylene, polyoxyalkylene, or hydroxyalkylene group, or combination thereof. R$^1$, R$^2$ and R$^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in R$^1$, R$^2$ and R$^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic conditioning polymer is selected from cationic cellulose and cationic guar derivatives. Particularly preferred cationic polymers are JAGUAR C13S, JAGUAR 15, JAGUAR C17 and JAGUAR C16 and JAGUAR C162.

The cationic conditioning polymer will generally be present in compositions of the invention at levels of from 0.01 to 5 preferably from 0.05 to 1, more preferably from 0.08 to 0.5 wt %.

CONDITIONER COMPOSITIONS

Compositions in accordance with the invention may also be formulated as conditioners for the treatment of hair (typically after shampooing) and subsequent rinsing.

CONDITIONING SURFACTANT

Such a conditioner will comprise one or more conditioning surfactants which are cosmetically acceptable and suitable for topical application to the hair.

Suitable conditioning surfactants are selected from cationic surfactants, used singly or in admixture.

Cationic surfactants useful in compositions of the invention contain amino or quaternary ammonium hydrophilic moieties which are positively charged when dissolved in the aqueous composition of the present invention.

Examples of suitable cationic surfactants are those corresponding to the general formula:

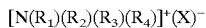

in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for conditioner compositions of the present invention are monoalkyl quaternary ammonium compounds in which the alkyl chain length is C8 to C14.

Suitable examples of such materials correspond to the general formula:

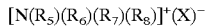

in which $R_5$ is a hydrocarbyl chain having 8 to 14 carbon atoms or a functionalised hydrocarbyl chain with 8 to 14 carbon atoms and containing ether, ester, amido or amino moieties present as substituents or as linkages in the radical chain, and $R_6$, $R_7$ and $R_8$ are independently selected from (a) hydrocarbyl chains of from 1 to about 4 carbon atoms, or (b) functionalised hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate, and alkylsulphate radicals.

The functionalised hydrocarbyl chains (b) may suitably contain one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof.

Preferably the hydrocarbyl chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of C8 to C12 hydrocarbyl chains.

Typical monoalkyl quaternary ammonium compounds of the above general formula for use in shampoo compositions of the invention include:

(i) lauryl trimethylammonium chloride (available commercially as Arguad C35 ex-Akzo); cocodimethyl benzyl ammonium chloride (available commercially as Arquad DMCB-80 ex-Akzo)

(ii) compounds of the general formula:

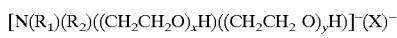

in which:

x+y is an integer from 2 to 20;

$R_1$ is a hydrocarbyl chain having 8 to 14, preferably 12 to 14, most preferably 12 carbon atoms or a functionalised hydrocarbyl chain with 8 to 14, preferably 12 to 14, most preferably 12 carbon atoms and containing ether, ester, amido or amino moieties present as substituents or as linkages in the radical chain;

$R_2$ is a $C_1$–$C_3$ alkyl group or benzyl group, preferably methyl, and

X is a salt-forming anion such as those selected from halogen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such as PEG-2 cocomonium chloride (available commercially as Ethoquad C12 ex-Akzo Nobel); PEG-2 cocobenzyl ammonium chloride (available commercially as Ethoquad CB/12 ex-Akzo Nobel); PEG-5 cocomonium methosulphate (available commercially as Rewoquat CPEM ex-Rewo); PEG-15 cocomonium chloride (available commercially as Ethoquad C/25 ex-Akzo); PEG-2 oleamonium chloride (available commercially as Ethoquad O/12 PG ex Akzo Nobel).

(iii) compounds of the general formula:

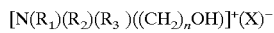

in which:

n is an integer from 1 to 4, preferably 2;

$R_1$ is a hydrocarbyl chain having 8 to 14, preferably 12 to 14, most preferably 12 carbon atoms;

$R_2$ and $R_3$ are independently selected from $C_1$–$C_3$ alkyl groups, and are preferably methyl, and X is a salt-forming anion such as those selected from halogen, (e.g. chloride, bromide), acetate, citrate, lactate, glycolate, phosphate nitrate, sulphate, and alkylsulphate radicals.

Suitable examples are lauryldimethylhydroxyethylammonium chloride (available commercially as Prapagen HY ex-Clariant)

Mixtures of any of the foregoing cationic surfactants compounds may also be suitable.

Examples of suitable cationic surfactants include:

quaternary ammonium chlorides, e.g. alkyltrimethylammonium chlorides wherein the alkyl group has from about 8 to 22 carbon atoms, for example octyltrimethylammonium chloride, dodecyltrimethylammonium chloride, hexadecyltrimethylammonium chloride, cetyltrimethylammonium chloride, octyldimethylbenzylammonium chloride, decyldimethylbenzylammonium chloride, stearyldi-methylbenzylammonium chloride, didodecyldimethylammonium chloride, dioctadecyldimethylammonium chloride, tallow trimethylammonium chloride, cocotrimethylammonium chloride, and the corresponding salts thereof, e.g., bromides, hydroxides. Cetylpyridinium chloride or salts thereof, e.g., chloride Quaternium –5

Quaternium –31

Quaternium –18 and mixtures thereof.

In the conditioners of the invention, the level of cationic surfactant is preferably from 0.01 to 10, more preferably 0.05 to 5, most preferably 0.1 to 2 wt % of the total compositions.

Fatty Alcohol Material

Conditioner compositions of the invention preferably additionally comprise a fatty alcohol material. The combined use of fatty alcohol materials and cationic surfactants in conditioning compositions is believed to be especially advantageous, because this leads to the formation of a lamellar phase, in which the cationic surfactant is dispersed.

By "fatty alcohol material" is meant a fatty alcohol, an alkoxylated fatty alcohol, or a mixture thereof.

Representative fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty alcohol material in conditioners of the invention is suitably from 0.01 to 15, preferably from 0.1 to 10, and more preferably from 0.1 to 5 wt %. The weight ratio of cationic surfactant to fatty alcohol is suitably from 10:1 to 1:10, preferably from 4:1 to 1:8, optimally from 1:1 to 1:7, for example 1:3.

Conditioner compositions of the invention can also contain a cationic polymer. Suitable cationic polymers are described hereinabove in relation to shampoo compositions.

OPTIONAL INGREDIENTS

Suspending Agents

In a preferred embodiment, the hair treatment composition, especially if it is a shampoo composition, further comprises from 0.1 to 5 wt % of a suspending agent for the coated particles. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol (trade mark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

The suspending agent for the coated particles is preferably a polymeric suspending agent.

Conditioning Agents

The compositions of this invention can also contain one or more conditioning agents selected from silicone conditioning agents and non-silicone oily conditioning agents.

When conditioning agent is present in the hair treatment compositions in droplet form, the droplets may be liquid, semi-solid or solid in nature, so long as they are substantially uniformly dispersed in the fully formulated product. Any droplets of oily conditioning agent are preferably present as either liquid or semi-solid droplets, more preferably as liquid droplets.

Silicone Conditioning Agents

The compositions of the invention can contain, emulsified droplets of a silicone conditioning agent, for enhancing conditioning performance. The silicone is insoluble in the aqueous matrix of the composition and so is present in an emulsified form, with the silicone present as dispersed droplets.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188. These materials can impart body, volume and stylability to hair, as well as good wet and dry conditioning.

The viscosity of the emulsified silicone itself (not the emulsion or the final hair conditioning composition) is typically at least 10,000 cst. In general we have found that conditioning performance increases with increased viscosity. Accordingly, the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in the shampoo compositions of the invention will typically have an average silicone droplet size in the composition of less than 30, preferably less than 20, more preferably less than 10 $\mu$m. We have found that reducing the droplet size generally improves conditioning performance. Most preferably the average silicone droplet size of the emulsified silicone in the composition is less than 2 $\mu$m, ideally it ranges from 0.01 to 1 $\mu$m. Silicone emulsions having a average silicone droplet size of $\leq 0.15$ $\mu$m are generally termed microemulsions.

Suitable silicone emulsions for use in the invention are also commercially available in a pre-emulsified form.

Examples of suitable pre-formed emulsions include emulsions DC2-1766, DC2-1784, and microemulsions DC2-1865 and DC2-1870, all available from Dow Corning. These are all emulsions/microemulsions of dimethiconol. Cross-linked silicone gums are also available in a pre-emulsified form, which is advantageous for ease of formulation. A preferred example is the material available from Dow Corning as DC X2-1787, which is an emulsion of cross-linked dimethiconol gum. A further preferred example is the material available from Dow Corning as DC X2-1391, which is a microemulsion of cross-linked dimethiconol gum.

A further preferred class of silicones for inclusion in shampoos and conditioners of the invention are amino functional silicones. By "amino functional silicone" is meant a silicone containing at least one primary, secondary or tertiary amine group, or a quaternary ammonium group.

Examples of suitable amino functional silicones include:
(i) polysiloxanes having the CTFA designation "amodimethicone", and the general formula:

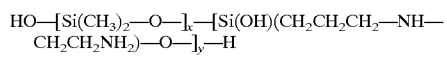

in which x and y are numbers depending on the molecular weight of the polymer, generally such that the molecular weight is between about 5,000 and 500,000

(ii) polysiloxanes having the general formula:

in which:
G is selected from H, phenyl, OH or $C_{1-8}$ alkyl, e.g. methyl;
a is 0 or an integer from 1 to 3, preferably 0;
b is 0 or 1, preferably 1;
m and n are numbers such that (m+n) can range from 1 to 2000, preferably from 50 to 150;
m is a number from 1 to 2000, preferably from 1 to 10;
n is a number from 0 to 1999, preferably from 49 to 149, and
R' is a monovalent radical of formula $-C_qH_{2q}L$ in which q is a number from 2 to 8 and L is an aminofunctional group selected from the following:

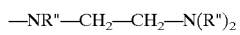

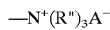

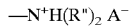

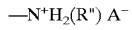

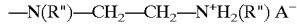

in which R" is selected from H, phenyl, benzyl, or a saturated monovalent hydrocarbon radical, e.g. $C_{1-20}$ alkyl, and A is a halide ion, e.g. chloride or bromide.

Suitable amino functional silicones corresponding to the above formula include those polysiloxanes termed "trimethylsilylamodimethicone" as depicted below, and which are sufficiently water insoluble so as to be useful in compositions of the invention:

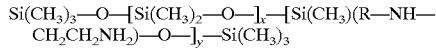

wherein x+y is a number from about 50 to about 500, and wherein R is an alkylene group having from 2 to 5 carbon atoms. Preferably, the number x+y is in the range of from about 100 to about 300.

(iii) quaternary silicone polymers having the general formula:

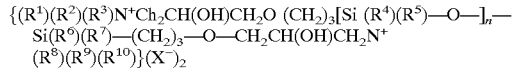

wherein $R^1$ and $R^{10}$ may be the same or different and may be independently selected from H, saturated or unsaturated long or short chain alk(en)yl, branched chain alk(en)yl and $C_5$–$C_8$ cyclic ring systems;

$R^2$ thru' $R^9$ may be the same or different and may be independently selected from H, straight or branched chain lower alk(en)yl, and $C_5$–$C_8$ cyclic ring systems;

n is a number within the range of about 60 to about 120, preferably about 80, and $x^-$ is preferably acetate, but may instead be for example halide, organic carboxylate, organic sulphonate or the like. Suitable quaternary silicone polymers of this class are described in EP-A-0 530 974.

Amino functional silicones suitable for use in shampoos and conditioners of the invention will typically have a mole % amine functionality in the range of from about 0.1 to about 8.0 mole %, preferably from about 0.1 to about 5.0 mole %, most preferably from about 0.1 to about 2.0 mole %. In general the amine concentration should not exceed about 8.0 mole % since we have found that too high an amine concentration can be detrimental to total silicone deposition and therefore conditioning performance.

The viscosity of the amino functional silicone is not particularly critical and can suitably range from about 100 to about 500,000 cst.

Specific examples of amino functional silicones suitable or use in the invention are the aminosilicone oils DC2-8220, DC2-8166, DC2-8466, and DC2-8950-114 (all Dow Corning, and GE 1149-75, (ex General Electric Silicones)

Also suitable are emulsions of amino functional silicone oils with non ionic and/or cationic surfactant.

Suitably such pre-formed emulsions will have an average amino functional silicone droplet size in the shampoo composition of less than 30, preferably less than 20, more preferably less than 10 μm. Again, we have found that reducing the droplet size generally improves conditioning performance. Most preferably the average amino functional silicone droplet size in the composition is less than 2 μm ideally it ranges from 0.01 to 1 μm.

Pre-formed emulsions of amino functional silicone are also available from suppliers of silicone oils such as Dow Corning and General Electric. Specific examples include DC929 Cationic Emulsion, DC939 Cationic Emulsion, and the non-ionic emulsions DC2-7224, DC2-8467, DC2-8177 and DC2-8154 (all ex Dow Corning).

An example of a quaternary silicone polymer useful in the present invention is the material K3474, ex Goldschmidt.

For shampoo compositions according to the invention intended for he treatment of "mixed" hair (i.e. greasy roots and dry ends), it is particularly preferred to use a combination of amino functional and non-amino functional silicone in compositions of the invention, especially when these are in the form of shampoo compositions. In such a case, the weight ratio of amino functional silicone to non-amino functional silicone will typically range from 1:2 to 1:20, preferably 1:3 to 1:20, more preferably 1:3 to 1:8.

The total amount of silicone incorporated into compositions of the invention depends on the level of conditioning desired and the material used. A preferred amount is from 0.01 to 10 wt % although these limits are not absolute. The lower limit is determined by the minimum level to achieve conditioning and the upper limit by the maximum level to avoid making the hair and/or skin unacceptably greasy.

We have found that a total amount of silicone of from 0.3 to 5, preferably 0.5 to 3 wt % is a suitable level.

The viscosity of silicones and silicone emulsions can be measures by means of a glass capillary viscometer as set out further in Dow Corning Corporate Test Method CTM004, Jul. 20, 1970.

In compositions comprising silicone, it is preferred that a suspending agent for the silicone also be present. Suitable suspending agents are as described hereinabove.

(ii) Non-silicone Oily Conditioning Components

Compositions according to the present invention may also comprise a dispersed, non-volatile, water-insoluble oily conditioning agent.

This component will be dispersed in the composition in the form of droplets, which form a separate, discontinues phase from the aqueous, continuous phase of the composition. In other words, the oily conditioning agent will be present in the shampoo composition in the form of an oil-in-water emulsion.

By "insoluble" is meant that the material is not soluble in water (distilled or equivalent) at a concentration of 0.1% (w/w), at 250° C.

Suitably, the $D_{3,2}$ average droplet size of the oily conditioning component is at least 0.4, preferably at least 0.8, and more preferably at least 1 μm. Additionally, the $D_{3,2}$ average droplet size of the oily conditioning component is preferably no greater than 10, more preferably no greater 8, more preferably no greater than 5, yet more preferably no greater than 4, and most preferably no greater than 3.5 μm.

The oily conditioning agent may suitably be selected from oily or fatty materials, and mixtures thereof.

Oily or Fatty materials are preferred conditioning agents in the shampoo compositions of the invention for adding shine to the hair and also enhancing dry combing and dry hair feel.

Preferred oily and fatty materials will generally have a viscosity of less than 5 Pa.s, more preferably less than 1 Pa.s, and most preferably less than 0.5 Pa.s, e.g. 0.1 Pa.s and under as measured at 25° C. with a Brookfield Viscometer (e.g. Brookfield RV) using spindle 3 operating at 100 rpm.

Oily and fatty materials with higher viscosities may be used. For example, materials with viscosities as high as 65 Pa.s may be used. The viscosity of such materials (i.e. materials with viscosities of 5 Pa.s and greater) can be measured by means of a glass capillary viscometer as set out further in Dow Corning Corporate Test Method CTM004, Jul. 2, 1970.

Suitable oily or fatty materials are selected from hydrocarbon oils, fatty esters and mixtures thereof.

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 30 carbon atoms. Branched chain hydrocarbon oils can and typically may contain higher numbers of carbon atoms. Also suitable are polymeric hydrocarbons of alkenyl monomers, such as $C_2$–$C_6$ alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 2000, preferably from about 200 to about 1000, more preferably from about 300 to about 600.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, sold by Permethyl Corporation. A further example of a hydrocarbon polymer is polybutene, such as the copolymer of isobutylene and butene. A commercially available material of this type is L-14 polybutene from Amoco Chemical Co. (Chicago, Ill., U.S.A.).

Particularly preferred hydrocarbon oils are the various grades of mineral oils. Mineral oils are clear oily liquids obtained from petroleum oil, from which waxes have been removed, and the more volatile fractions removed by distillation. The fraction distilling between 250° C. to 300° C. is termed mineral oil, and it consists of a mixture of hydrocarbons ranging from $C_{16}H_{34}$ to $C_{21}H_{44}$. Suitable commercially available materials of this type include Sirius M85 and Sirius M125, all available from Silkolene. Suitable fatty esters are characterised by having at least 10 carbon atoms, and include esters with hydrocarbyl chains derived from fatty acids or alcohols, e.g., monocarboxylic acid esters, polyhydric alcohol esters, and di- and tricarboxylic acid esters. The hydrocarbyl radicals of the fatty esters hereof can also include or have covalently bonded thereto other compatible functionalities, such as amides and alkoxy moieties, such as ethoxy or ether linkages.

Monocarboxylic acid esters include esters of alcohols and/or acids of the formula R'COOR in which R' and R independently denote alkyl or alkenyl radicals and the sum of carbon atoms in R' and R is at least 10, preferably at least 20.

Specific examples include, for example, alkyl and alkenyl esters of fatty acids having aliphatic chains with from about 10 to about 22 carbon atoms, and alkyl and/or alkenyl fatty alcohol carboxylic acid esters having an alkyl and/or alkenyl alcohol-derived aliphatic chain with about 10 to about 22 carbon atoms, benzoate esters of fatty alcohols having from about 12 to 20 carbon atoms.

The monocarboxylic acid ester need not necessarily contain at least one chain with at least 10 carbon atoms, so long as the total number of aliphatic chain carbon atoms is at least 10. Examples include isopropyl isostearae, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Di- and trialkyl and alkenyl esters of carboxylic acids can also be used. These include, for example, esters of $C_4$–$C_8$ dicarboxylic acids such as $C_1$–$C_{22}$ esters (preferably $C_1$–$C_6$) of succinic acid, glutaric acid, adipic acid, hexanoic acid, heptanoic acid, and octanoic acid. Examples include diisopropyl adipate, diisohexyl adipate, and diisopropyl sebacate. Other specific examples include isocetyl stearoyl stearate, and tristearyl citrate.

Polyhydric alcohol esters include alkylene glycol esters, for example ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol monostearate, ethoxylated propylene glycol monostearate, polyglycerol polyfatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters and mono-, di-and triglycerides.

Particularly preferred fatty esters are mono-, di- and triglycerides, more specifically the mono-, di-, and tri-esters of glycerol and long chain carboxylic acids such as $C_1$–$C_{22}$ carboxylic acids. A variety of these types of materials can be obtained from vegetable and animal fats and oils, such as coconut oil, castor oil, safflower oil, sunflower oil, cottonseed oil, corn oil, olive oil, cod liver oil, almond oil, avocado oil, palm oil, sesame oil, peanut oil, lanolin and soybean oil. Synthetic oils include triolein and tristearin glyceryl dilaurate.

Specific examples of preferred materials include cocoa butter, palm stearin, sunflower oil, soyabean oil and coconut oil.

The oily or fatty material is suitably present at a level of from 0.05 to 10, preferably from 0.2 to 5, more preferably from about 0.5 to 3 wt %.

The compositions of this invention preferably contain no more than 3 wt % of a styling polymer, more preferably less than 1% of a styling polymer, preferably contain less than 0.1% by weight a styling polymer, and optimally are free of styling polymer.

In hair treatment compositions containing a conditioning agent, it is preferred that a cationic polymer also be present.

Adjuvants

The compositions of the present invention may also contain adjuvants suitable for hair care. Generally such ingredients are included individually at a level of up to 2, preferably up to 1 wt % of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine.

(ii) hair fibre benefit agents. Examples are:
ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

The invention will now be further illustrated by the following, non-limiting Examples.

EXAMPLES

Coated particles comprising solid silica cores and polystyrene coating polymer were used as described in Pyun et al. (2001) *Polym. Prepr.* (*Am. Chem. Soc., Div. Polym. Chem.*), Vol. 42(1), 223. The solid silica cores had an average particle size of 15 nm and the coated particles had an average particle size of 30 nm.

The coated particles were assessed in a half head mannequin test. The mannequin hair was washed twice with 3 g of a conventional shampoo and treated with 3 g of an off the shelf rinse-off conditioner once. The hair was divided in two and 5 ml of an aqueous dispersion of the coated particles (at a level of about 500 ppm) applied all over half the hair. This was left on. The hair was allowed to dry and the two halves of the hair were assessed by a trained analyst.

The half head treated with the coated particles demonstrated a higher root lift than the half head which had not been treated.

The following formulation was prepared. It gave good root lift when compared with a similar formulation without the coated core shell silica.

| DESCRIPTION | wt. % |
| --- | --- |
| Liq. citric acid, 50% active | 0.24500 |
| Stearamidopropyl dimethylamine, 100% active | 0.75000 |
| PEG-2 oleamonium chloride & propylene glycol | 2.00000 |
| Behenyl TMAMS and cetearyl alcohol, 25% active | 3.00000 |
| Stearyl alcohol, USP grade 100% active | 2.00000 |
| Disodium EDTA, 100% active | 0.10000 |
| Preservative | 0.14 |
| Core shell silica[1] - coated | 1.00000 |
| Perfume | 0.60000 |
| Water | to 100 |

[1]Core shell silica as described above.

What is claimed is:

1. An aqueous hair treatment composition comprising from 0.01 to 10% by weight of coated particles comprising:
    (a) a solid core having a D3,2 average particle size in the range from 10 to 700 nm, and
    (b) a coating polymer covalently bonded to the solid core, the coating polymer being selected from the group consisting of anionic, nonionic and amphoteric polymers and ranging from about 20 to 95% by total weight of the coated particles; and wherein the aqueous hair treatment composition is a shampoo further comprising in an amount from 5 to 50% by weight of at least one cleansing surfactant selected from the group consisting of anionic, nonionic, amphoteric and zwitterionic surfactants and mixtures thereof, and further comprising a cationic polymer.

2. A composition according to claim 1, in which the weight ratio of the solid core to the coating polymer is in the range from 5:1 to 2:1.

3. A composition according to claim 1, in which the solid core comprises material selected from polymers, alumina, alumin silicate and colloidal metals.

4. A composition according to claim 1, in which the solid core is a colloidal silica.

5. A composition according to claim 1, in which the solid core particles have a Youngs Modulus of more than 0.01 GPa.

6. A method of imparting body to hair according to claim 1 comprising:
    i) providing the aqueous hair treatment composition:
    ii) applying the composition to hair;
    iii) optionally rinsing the hair; and
    iv) drying and styling the hair.

7. A composition according to claim 1 wherein the coating polymer has less than 5 weight percent silicone units.

8. A composition according to claim 1 wherein the coated particles are present in an amount from 0.01 to 0.5% by weight of the composition.

9. An aqueous hair treatment composition comprising from 0.01 to 10% by weight of coated particles comprising:
    (a) a solid core having a D3,2 average particle size in the range from 10 to 700 nm; and
    (b) a coating polymer covalently bonded to the solid core, the coating polymer being selected from the group consisting of anionic, nonionic and amphoteric polymers and ranging from about 20 to 95% by total weight of the coated particles; and
    wherein the composition is a conditioner further comprising from 0.01 to 10% by weight of at least one conditioning surfactant and from 0.01 to 15% by weight of a fatty alcohol material.

10. A composition according to claim 9, in which the weight ratio of the solid core to the coating polymer is in the range from 5:1 to 2:1.

11. A composition according to claim 9, in which the solid core comprises material selected from polymers, alumina, aluminum silicate and colloidal metals.

12. A composition according to claim 9, in which the solid core is a colloidal silica.

13. A composition according to claim 9, in which the solid core particles have a Youngs Modulus of more than 0.01 Gpa.

* * * * *